United States Patent [19]

Mecca

[11] Patent Number: 4,690,140
[45] Date of Patent: Sep. 1, 1987

[54] ARTERIAL REGENERATOR

[76] Inventor: John Mecca, 110 Whittier Dr., San Remo, N.Y. 11754

[21] Appl. No.: 846,727

[22] Filed: Apr. 1, 1986

[51] Int. Cl.⁴ ............................................ A61B 17/32
[52] U.S. Cl. ....................................... 128/305; 128/6; 128/305.1; 604/22
[58] Field of Search ..................... 128/305, 304, 348.1, 128/305.1, 6; 604/22

[56] References Cited

U.S. PATENT DOCUMENTS 4,418,688 12/1983 Loeb ........................................ 128/6
4,589,412 5/1986 Kensey ................................. 128/305

FOREIGN PATENT DOCUMENTS

2804015 8/1979 Fed. Rep. of Germany ...... 128/305

Primary Examiner—Michael H. Thaler
Attorney, Agent, or Firm—Leonard Belkin

[57] ABSTRACT

Apparatus mounted on the end of a catheter for use in the removal of deposits lining the interior wall of a blood vessel comprising an endoscopic tube for lighting and viewing the region of the deposits and mechanism for controlling its movement. A rotating cutting device is provided. Clear liquid is circulated around the endoscopic tube to insure proper visibility while provision is made to bypass some of the liquid to suck in and remove the debris.

7 Claims, 11 Drawing Figures

ARTERIAL REGENERATOR

BACKGROUND OF THE INVENTION

1. Field of the invention

The present invention relates to the removal of tissue in the body, particularly arterial sclerosis deposits, tumor tissue, throat and nasal obstructions; Also intercranial and body cavity tissue removal. All without surgical dissection of the body by merely using a specialized tool at the end of a catheter tube.

2. Prior Art

With the increased need to eliminate opening the chest cavity and do heart bypass surgery to the cardiovascular system; As well as angio plasty done by baloon catheterization as a stopgap measure to stem the advance of arterial scelerosis blockages.

The typical techniques previously used are a catheter with a baloon mounted at the end that is pushed into the restriction and then expanded where upon deflation the artery wall would remain open if it did not crack, burst, or the baloon tip may deviate from it's course and puncture the artery wall requiring a chest cavity incision opening and subsequent repair. Can also be used to eliminate the need for coronary bypass grafts.

The present invention substantially resolves these problems disclosed by prior art which exist at sites of constrictions, and unwanted tissue from a desired area.

The tool for removing tissue consists of a spinning drill head mounted at the end of a catheter tube tip. At the tip of the drill face slots are cut into the top surface parallel to the blades and convey debris cut free down these slots to a venturi constriction area where a stream of high velocity solution causes a vacuum action to suck the debris into the slotted holes next to the cutting blades, the stream of high velocity solution then entrains the debris at the constriction of the venturi and enters the exhaust cavity of the venturi cavity where it is deflected down into vanes milled into the cutting head causing it to rotate from the stream of liquid against the turbine reaction blades surface for continual cutting.

SUMMARY OF THE INVENTION

The present invention comprises a spinning drill that has cutting edges at it's tip and is caused to spin from an appropriate liquid solution that impinges upon turbine like spiral vanes. Initially a liquid solution is sent through a venturi constriction causing a partial vacuum to draw debris from the cutting blade edge into the cutting head through the slots parallel to the cutting edges and subsequently impinges upon the turbine impellers causing the drill tip to revolve from it's impaction.

A lead in needle is alternately utilized as an endoscopic optical targeter, and as an auger lead in needle that is projected from the drill head and guides the cutter head into the work site by sticking into the target.

It is therefore an object of the present invention to provide removal of obstructing tissue using a rotating cutting head at the tip of a catheter.

It is yet another object of the present invention to utilize pressurized solution to be fed through the catheter to the revolvable drill tip head and inpinge upon vanes not unlike turbine blades to cause the drill tip to revolve and shear off the desired material, therefore eliminating any need for a cable to revolve or reciprocate to drive the cutter head.

It is yet another object of the present invention to utilize the stream of appropriate solution that causes the drill head to revolve from reaction against the turbine like blades that has come from the venturi cavity to be used also to create the vacuum that sucks from the slot at the cutting edge to remove sheared material into the liquid stream for removal.

It is yet another object of the present invention to utilize an endoscopic fiber needle to allow viewing into the area of work and to alternately be used as a needle that extends and sticks into the tissue to guide the cutter head.

It is yet another object of the present invention to provide for angiographic dye to further define the tissue area, during the procedure as operators view by means of fluoroscopy dye bled through the hole the endoscopic needle alternately protrudes from.

The novel features which are believed to be characteristic of the invention, both to it's organization and method of facilitating the removal of tissue, together with further objectives and advantages thereof will be better understood from the following description considered in connection with the accompanying drawings in which a presently preffered embodiment of the invention is illustrated by way of example. It is to be expressly understood that the drawings are for the purpose of illustration and description only, and is not intended as a definition of the limits of the invention.

BRIEF DESCRIPTION OF THE INVENTION

DESCRIPTION OF THE PRESENTLY PREFERRED EMBODIMENT

Figure 1:
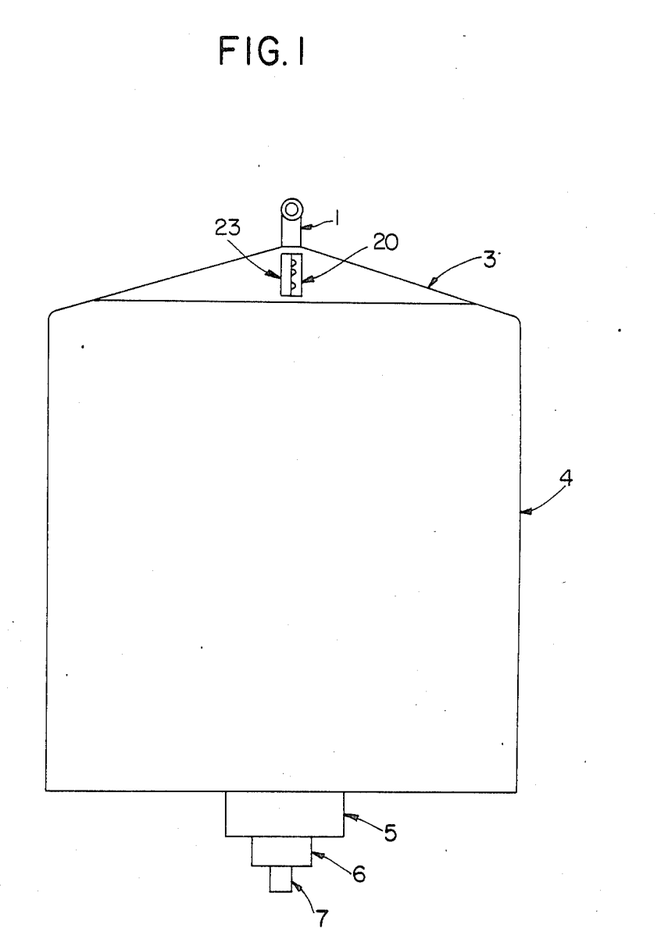
FIG. 1 is a side view of the cylinderical body of the cutting head in the fully assembled state ready to attach to the end of the catheter tube that will lead it to it's destination in the body of the work to be operated upon.

An understanding of the present invention can best be gained by reference to FIG. 1 wherein a side view of the unit is shown, the tissue remover being generally designated by numeral 4. As stated previously the present arterial restorer is to be used to allow removal of material within bodies of material that require immediate removal of tissue from the site of the vutting blade and communicated outside the body to be worked within without contamination of the interior with the material being removed. In this context, stationary main body cylinder 4 provides the outer surface that houses within it a rotating cutting cylinder 3. Integrally mounted on the rotating cylinder face are cutting blade edges 20, adjacent and parallel to the cutting edge is the partial vacuum slot 23 that sucks matter sheared by the blades into the rotating cylinder. Numeral 1 represents the endoscopic and illuminating guide needle. At the bottom end of the cylinder 5 is the input tube for suitable operating liquid. Within input tube 5 is tube 6 having a completely seperate source of liquid of the same nature as tube 5. This tube 6 is used as a pressure line to alternately cause the endoscopic needle to be actuated in and out of the front cutting surface. The needle 1 shaft within the tube 6 has an action not unlike a cylinder head within a cylinder wall 6. The needle can be projected and withdrawn at the discretion of the operator applying positive or negative pressure on this self contained liquid line. Numeral 7 represents the endoscopic and illuminating line leading out of the body to the operator viewing screen.

Figure 2:
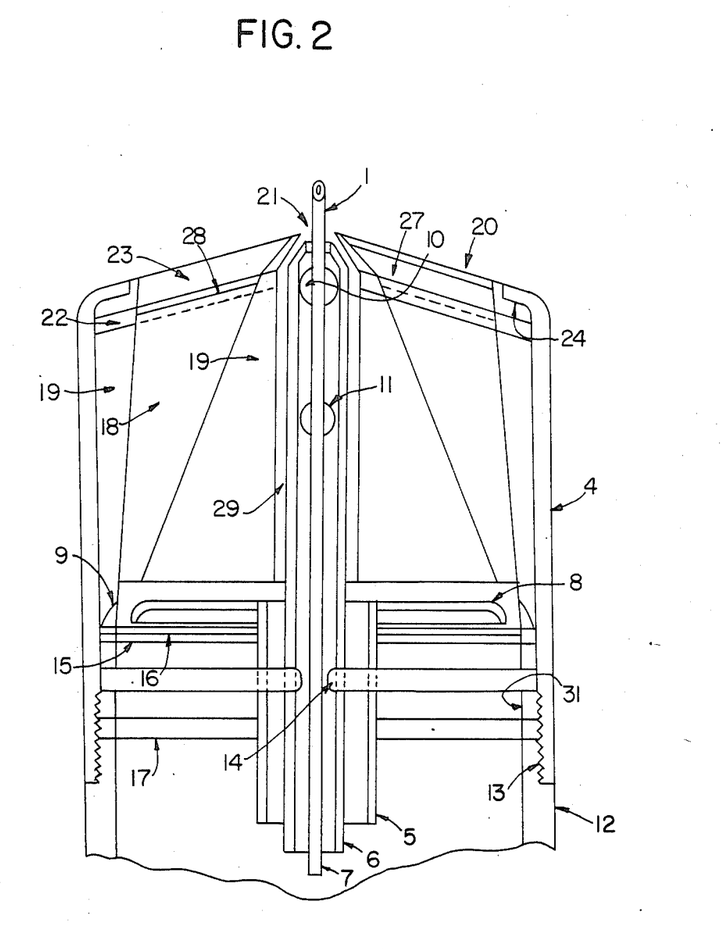
FIG. 2 is a cross section view of FIG. 1 showing it's cylinder shape divided down it's axis exposing the parts within and their relation to one another.

Referring to FIG. 2 shows a crossection down the axis of the cylinder showing the parts, channels, and mechanisms in detail; numeral 1 represents the working end of endoscopic and illuminating optics terminating at a point for the purpose of alternately being pushed into the work and retracting to promote stable and concise cutting of only that material desired. In order to facilitate the alternate projection and retraction of endoscopic needle 1, a spherical ball plug 10 is stationarily upon the needle shaft and it completely blocks the positive and negative liquid pressure in tube 6 for needle activation. This ball plug 10 acts as a piston carrying the attached needle forward and back at endoscopic operator's discretion. Numeral 11 is also a stationary sphere mounted on the needle shaft but does not completely block liquid flow, as it is used to keep the needle from deflecting and facilitates cleaning. Boths phere piston plug and guide are spherical to minimize surface area contact against the tube wall of 6. In order to better permit seeing into the cavity numeral 21 represents an orafice for a predetermined bleeding of the appropriate organ compatiable optically clear fluid to exit into the area to be examined. This is to say the clear liquid metered out the orifice 21 into the area to be examined for tissue removal acts to fill the immediate area. The needle's optic window is near, with a pocket of clear liquid to observe for targeting the point of impact of needle tip for injection at discretion of operator. Numeral 14 is a crossbrace support for tubes 5 and 6, while also doubling as a mechanical stop to prevent sphere 11 from passing that constriction. The endoscopic tube that connectes this fluid driven cutter and carries input of fluid and suction elimination of waste is numeral 12. It is coupled to the seperate cutting head by threads numeral 13. The stationary input tube 5 terminates and is topped with a disc 8 which is attached there, creates a cavity that directs fluid into the turbine impeller contour 9 causing rotation of cylinder 19. Once fluid passes intersection of impellers it is directed down and into the evacuation catheter tube 12 for constant suction removal. The rotating cylinder 19 seats upon two washers 15 and 16 at it's bottom rim edge to allow sufficient play and reduce friction from compression when cutter head is pushed into the work surface. To facilitate fluid flow to the cutter blade it flows through hole 29 and leads to metered orifice 21 and also into channels 27. Numeral 22 is an opening of the channel to allow fluid to communicate as lubricant to bearing surfaces between stationary head 4 and rotating inner cylinder 19. This space that allows free rotation would be of appropriate tollerence to prevent friction and allow lubrication. Numeral 24 is a shoulder on the cutter face for retaining within 4. Numeral 20 is the cutter edge, parallel to it is the partial vacuum channel 23 communicates debris for removal from cutting blades shearing of work. Numeral 31 is a ring with threads on it's outer diameter and is used to position and set the play necessary for cylinder 19 free-play; the counter tightening setting of it's opposing ring 17 also threaded on it's outer diameter is used to tighten against ring 31 to prevent change of position and allow future adjustment.

Figure 3:
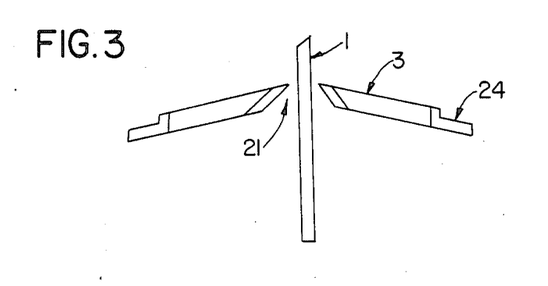
FIG. 3 is a cross section view of the cutting face down the axis of the cylinder.

Refering now to FIG. 3 is a crossection of cutter top face showing the needle 1, the front disc 3 that the cutters are integrally shaped upon, also seen is a close up of the metering orifice 21, and retainer shoulder permitting a flush bearing surface at the top of the device.

Figure 4:
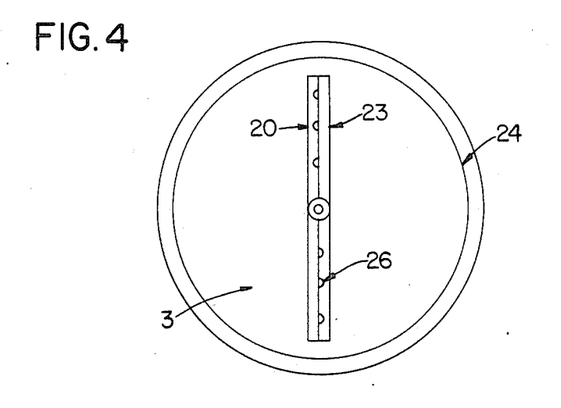
FIG. 4 is a top front view of the cylinders rotating cutting head showing cutting blades and input channels flanking the guide needle and bleed port at it's center, also demstrated are scallop ridges on the cutting blades to present a serrated cutting of the material desired.

Refering now to FIG. 4 is a top view of cutter face 3 showing cutter blade edges 20, adjacent evacuation channels 23, scalloped depression 26 to promote the further reduction in size of the sheared tissue and reduces any large sheets of tissue from forming that could block internal passages.

Figure 5:
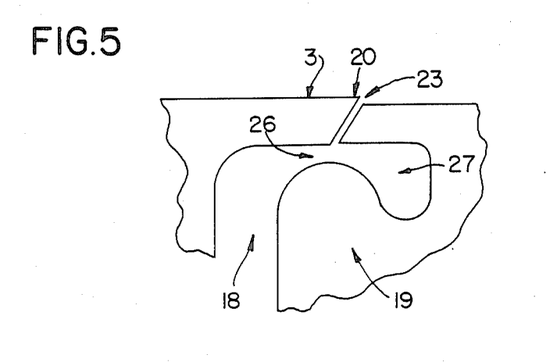
FIG. 5 is a crossection of the venturi cavity immediately under the cutting head responsible for sucking debris away from the cutting blade and into the cutting head, also detailed is the cutting edge ridge.

Referring to FIG. 5 shows a lengthwise crossection of the venturi chamber 26 adjacently connected by channel 23 to suction away debris being sheared by blades 20. Clear liquid comming up the central supply tube through channel 29 via input tube 5 is unrestricted in flow into channel 27; It's increased velocity through constriction 26 and subsequent exit into widening channel 18 through the body of the rotating cylinder 19 causes a vacuum at channel 23 for suction removal of debris cut by blades 20. Coupled to this suction force is the centrifugal reaction of the spinning cylinder in that channel 18 has it's wall at an incline that tapers to decrease throughout it's desent through cavity 18's length from the area of the cutting edges down to the turbine impeller bottom destination of fluid and debris where it reaches the inclines beginning.

Figure 6:
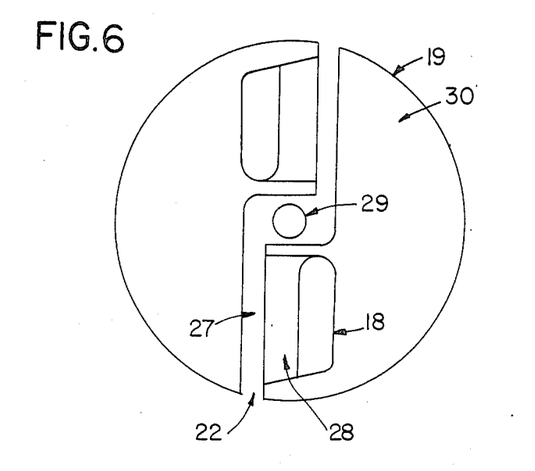
FIG. 6 is a crossection view of the top of the cylinder immediately under the cutting blades and shows the milled out channel configuration that represents the venturi input low pressure point of intersection with the port in the cutting face to suck in debris, and the output channel.

Refering now to FIG. 6 is a crossection of the rotating cylinder immediately beneath the cutter face where partial vacuum pressure shown previously in (FIG. 5. Numeral 28) connects to milled recess constriction 23 where velocity of fluid causes suction of debris. The fluid comes up through the hole 29 shown shaded to depict it's continuation all the way through the rotating cylinder 19 to it's bottom and from that point, and subsequently communicates to channel 27 and bearing lubrication feed hole 22. The fluid velocity from channel 27 increases across the smaller constriction depression 28, and subsequently flows now entraining debris down channel 18 which has a taper that through centrifugal force further helps sustain fluid directional flow down the incline. Numeral 30 represents the top most surface immediately under the cutter head surface. These two pieces are brazed or otherwise mated together to form the revolving cylinder cutter.

Figure 7:
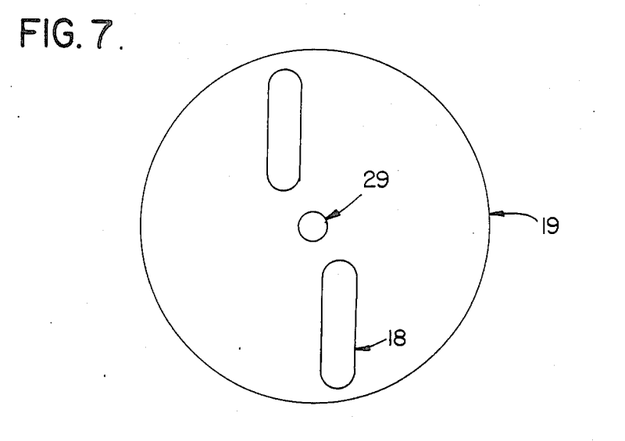
FIG. 7 is a top crossection view of the rotating body cylinder portion of the unit that shows the through holes to convey the input of fluid. The center hole is for output, and the oblong holes flanking the center are output through hole channels to carry away debris

Refering now to FIG. 7 shows a crossection of the cylinder 19 midway down it's total length showing through holes for input of fluid to cutting head comming from through hole 29, and then decending through hole 18, which also has the taper that causes the debris and liquid to flow down and away from the cutters due partly from the sentrifugal force. The debris laden liquids direction is compunded by exit pressure from venturi output side (27 shown in FIG. 6).

Figure 8:
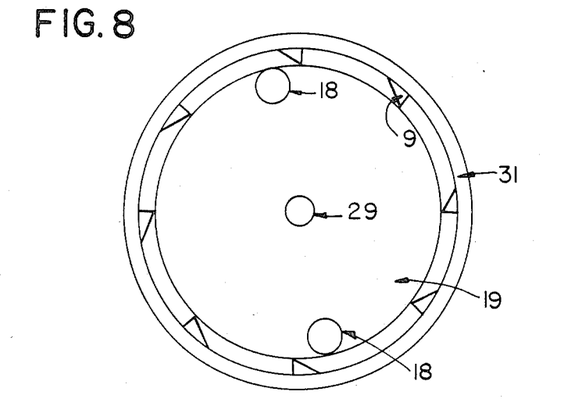
FIG. 8 shows a crossection view from the bottom end of the cylinder showing the continuation of through hole liquid conveyance channels and their termination at the end surface of the rotating portion of the device, also shown around the periphery are inclined planes which when impinged upon by the fluid acts as the blades of a turbine and imparts impetus to the rotating body by their being an integral part formed at the bottom edge of the rotating cylinder body.

Refering now to FIG. 8 shows input liquid through hole 29. Subsequent output and tapering through hole 18. Numeral 9 represents recessed bore into the body 19 that has the lip edge mill formed into impeller turbine blade incline shapes to be impinged upon by the flow of fluid, from the cavity created by (FIG. 2 numeral 8 washer disc's constraint of flow of fluid from input feed tube 5). Numeral 31 represents surface that (washers 15 and 16 in FIG. 2) would be placed upon for friction reduction.

Figure 9:
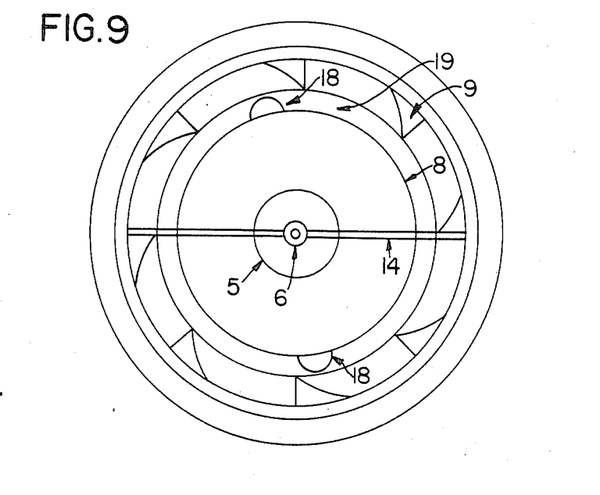
FIG. 9 shows a bottom end view of the cylinder demonstrating the position of the turbine rotated inner cylinder in relation to it's stationary cylinder that acts as a bearing wall sleeve at it's outside diameter. The stationary external wall shows it's connection to a stationary bridge crossing it's diameter and acting as a brace for the input tube for liquid; Also shown extended from this stationary bridge and at the end of the input line is a top view of the disc that centrally and partially covers the rotating body center, guiding the liquid from the central input point to the periphery and against the impeller turbine rotating body.

Refering now to FIG. 9 shows bottom end view with inlet flow and stationary support structure, numeral 18 shows outlet termination through hole emerging at the inner surface of the recessed bore face of numeral 19 facilitating the liquid flow comming in from tube 5 thereby entrained between end cylinder surface and deflection washer 8 directs fluid directly from feed line and bypassing through put channel to cutter head to impinge upon the turbine impeller 9 which is integrally formed into the lip edge surface of 19 to produce rotation of cylinder 19. To facilitate stationary positioning of the feed tube crossbrace 14 is brazed to it, and to the retractable needle tube 6 as well.

Figure 10:
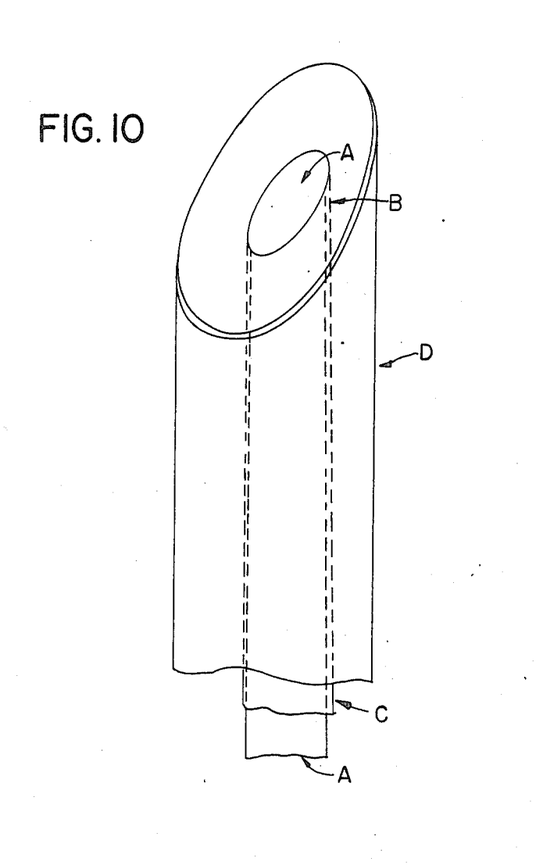
FIG. 10 shows a side view of the needle with delineation of the center axis cylinder within the multiple sheath covering representing an endoscopic fiber optic through which the operator can see into the cavity through it's open viewing end. The endoscopic inner sighting optic is within a surrounding coating of light carrying fiber optic material used to direct light into the area viewed. The diagonal angle shown at the tip where viewing and is labeled serves to act as a sharp needle and not unlike a pin tip and is used to be pushed into the material to be removed as needed.

Refering now to FIG. 10 is a top view of the needle and of the endoscopic illuminating needle guide, where letter a. is the optically plane surface viewing port that the work area is viewed from, letter be. is an opaque substance such as platinum that also acts as the leading point of the needle which could be applied to that surface by electrodeposition, letter c. is an opaque sheath surrounding the entire length of the cylinder representing the optic viewing needle.

The side view shows the endoscopic filiament a., and to prohibit light interference there is the platinum coat b., letter c. also is an opaque film sheath to prevent the light carrying fiber optic material c. from interferring with the image received by filiament a..

Figure 11:
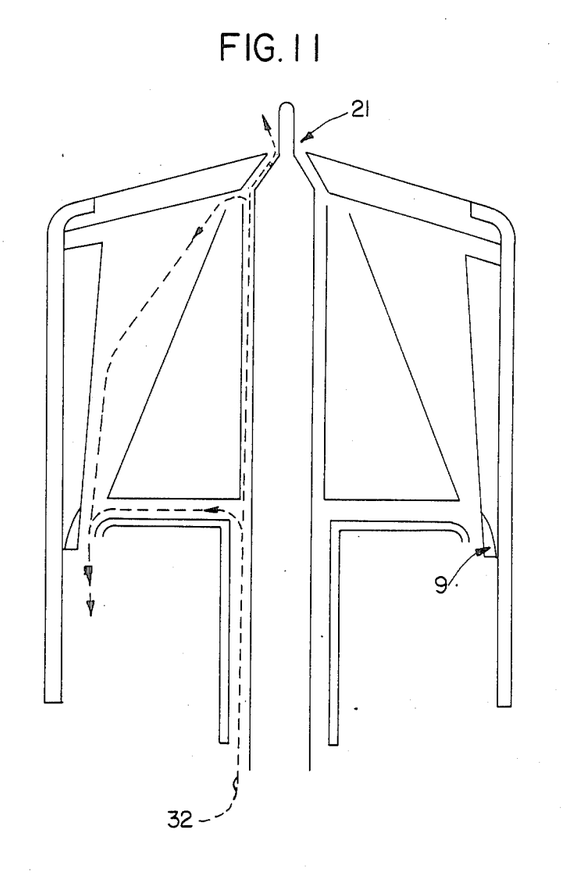
FIG. 11 shows a crossection down the axis of the cylinder with a clear indication of dotted lines and arrows depicting the flow of liquid through the various cavities and shows in a clearer way the turbine blade intersection reaction area and the overall flow pattern further described.

Refering to FIG. 11 is a cross section of the complete cylinder cutting head with dotted lines and arrows depicting the flow of liquid from the beginning input designated numeral 32 showing a flow pattern through the unit to clarify understanding, however due to complexity of cutter head vacuum action area the flow is shown simplified and the area not shown here is explained in FIG. 5 cross referenced to FIG. 6. The width of the device varies with the need.

I claim:

1. A cutter head assembly mounted on the end of a catheter for use in the removal of deposits lining the interior wall of a blood vessel and the like, comprising:
    (a) non-rotating cylinder means having an outer wall fitted to the inside wall of said vessel;
    (b) endoscopic tube means for lighting and viewing the region of said deposits adjacent said cutter head assembly, said endoscopic tube means extending from said catheter through said cylinder means and out through the end of said cylinder means facing said deposits to be removed;
    (c) means for effecting the controlled movement of said endoscopic tube means in forward and reverse directions so as to permit selective viewing of the deposits to be removed;
    (d) cutting means enclosed within the outer wall of said cylinder means on the end of the latter facing said deposits for rotation around said endoscopic tube means for dislodging said deposits;
    (e) means for circulating clear liquid around said endoscopic tube means for exposing the region forward of said cutting means for viewing prior to and during cutting action of said cutting means;
    (f) means within said cylinder means for bypassing a first portion of said clear liquid for use in causing rotation of said cutting means, said cutting means including vanes against which said liquid impinges for causing said rotation;
    (g) means within said cylinder means for utilizing a second portion of said liquid to effect the entrapment and removal of deposits being dislodged by said cutting means; and
    (h) means within said cutting means forming a venturi constriction past which the second portion of said liquid passes to cause suction in and removal through of the dislodged deposits.

2. The cutter head assembly of claim 1 in which said cutting means includes at least one radially extending slot forming said venturi restriction and having cutting blade means along one edge of said slot for directing deposits dislodged thereby during rotation into said slot for being carried away by liquid being sucked through said venturi constriction.

3. The cutter head assembly of claim 2 in which said venturi constriction opens within said rotating cutting means into a cavity having a wall sloping outwardly so that the effect of centrifugal force on the dislodged deposits therein is to facilitate movement along with the liquid flowing away from said venturi constriction.

4. The cutter head assembly of claim 3 having means to reunite the first and second portions of said clear liquid adjacent said vanes to prevent said dislodged deposits from clogging said vanes.

5. A cutter head assembly mounted on the end of a catheter for use in the removal of deposits lining the interior wall of a blood vessel and the like, comprising:
 (a) non-rotating cylinder means having an outer wall fitted to the inside wall of said vessel;
 (b) endoscopic tube means for lighting and viewing the region of said deposits adjacent said cutter head assembly, said endoscopic tube means extending from said catheter through said cylinder means and out through the end of said cylinder means facing said deposits to be removed;
 (c) means for effecting the controlled movement of said endoscopic tube means in forward and reverse directions so as to permit selective viewing of the deposits to be removed;
 (d) cutting means enclosed within the outer wall of said cylinder means on the end of the latter facing said deposits for rotation around said endoscopic tube means for dislodging said deposits;
 (e) means for circulating clear liquid around said endoscopic tube means for exposing the region forward of said cutting means for viewing prior to and during cutting action of said cutting means;
 (f) means within said cylinder means for bypassing a first portion of said clear liquid for use in causing rotation of said cutting means;
 (g) means within said cylinder means for utilizing a second portion of said liquid to effect the entrapment and removal of deposits being dislodged by said cutting means; and
 (h) said means for effecting movement of said endoscopic tube means including piston means actuated by a liquid for moving said endoscopic tube means.

6. The cutter head assembly of claim 5 in which said endoscopic tube means terminates in a tip having a diagonally oriented face from which light is directed and from which the region opposite said cutter head assembly is viewed.

7. The cutter head assembly of claim 6 in which said endoscopic tube means includes a central fiber optic cable coated with an opaque substance for delivering light to said region, said tube means surrounding said fiber optic cable being transparent for viewing said region, said tube means being coated with an opaque sheath.

* * * * *